(12) United States Patent
Yazdanfar et al.

(10) Patent No.: US 8,169,696 B2
(45) Date of Patent: May 1, 2012

(54) SYSTEMS FOR INTRAOPERATIVE NERVE IMAGING

(75) Inventors: Siavash Yazdanfar, Niskayuna, NY (US); Cristina Abucay Tan Hehir, Niskayuna, NY (US); Xinghua Wang, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 113 days.

(21) Appl. No.: 12/821,731

(22) Filed: Jun. 23, 2010

(65) Prior Publication Data

US 2010/0312122 A1 Dec. 9, 2010

Related U.S. Application Data (63) Continuation-in-part of application No. 12/694,820, filed on Jan. 27, 2010, and a continuation-in-part of application No. 12/543,785, filed on Aug. 19, 2009, now Pat. No. 7,885,011, and a continuation-in-part of application No. 12/478,300, filed on Jun. 4, 2009.

(51) Int. Cl.
   *G02B 21/06* (2006.01)
   *G02B 27/02* (2006.01)
   *A61B 6/00* (2006.01)
(52) U.S. Cl. ............... 359/385; 359/798; 600/476
(58) Field of Classification Search .......... 359/385, 359/618, 798; 600/476
See application file for complete search history.

(56) References Cited

U.S. PATENT DOCUMENTS

| | | | |
|---|---|---|---|
| 4,037,938 A | 7/1977 | Yamashita et al. | |
| 4,042,295 A | 8/1977 | Yamasita et al. | |
| 4,059,344 A | 11/1977 | Yamasita | |
| 5,493,441 A | 2/1996 | Chipper | |
| 5,543,966 A | 8/1996 | Meyers | |
| 5,563,966 A | 10/1996 | Ise et al. | |
| 5,612,818 A * | 3/1997 | Kumagai et al. | 359/385 |
| 5,691,847 A | 11/1997 | Chen | |
| 5,731,914 A | 3/1998 | Meyers | |
| 5,748,372 A | 5/1998 | Kitagawa | |
| 5,752,517 A | 5/1998 | Harman et al. | |
| 5,768,030 A | 6/1998 | Estelle et al. | |
| 5,880,879 A | 3/1999 | Foo | |
| 5,923,479 A | 7/1999 | Nagata | |
| 5,966,244 A | 10/1999 | Mukai et al. | |
| 5,978,159 A | 11/1999 | Kamo | |
| 6,034,819 A | 3/2000 | Ogata | |
| 6,088,322 A | 7/2000 | Broome et al. | |

(Continued)

FOREIGN PATENT DOCUMENTS

WO WO0224058 A2 3/2002

OTHER PUBLICATIONS

Wang et al., "Compact Instrument for Fluorescence Image-Guided Surgery", Journal of Biomedical Optics, vol. 15, No. 2, pp. 020509-1 to 020509-3, Mar./Apr. 2010. Boppart et al., "Optical Coherence Tomography for Neurosurgical Imaging of Human Intracortical Melanoma", Neurosurgery, vol. 43, No. 4, pp. 834-841, Oct. 1998.

*Primary Examiner* — William Choi
(74) *Attorney, Agent, or Firm* — Eileen W. Gallegher (57) ABSTRACT

Disclosed are systems for intraoperative nerve imaging using compact high collection power imaging devices for fluorescence and white light imaging of myelin basic protein (MBP) nerve imaging agents during open and minimally invasive surgery.

20 Claims, 6 Drawing Sheets

U.S. PATENT DOCUMENTS

| | | |
|---|---|---|
| 6,122,104 A | 9/2000 | Nakai |
| 6,618,205 B2 | 9/2003 | Murayama |
| 6,741,403 B2 | 5/2004 | Huang |
| 6,825,979 B2 | 11/2004 | Ogawa |
| 6,950,241 B1 | 9/2005 | Liang |
| 7,023,622 B2 | 4/2006 | Liang |
| 7,180,686 B2 | 2/2007 | Kato |
| 7,692,160 B2 | 4/2010 | Lee et al. |

* cited by examiner

SYSTEMS FOR INTRAOPERATIVE NERVE IMAGING

CROSS-REFERENCE TO RELATED APPLICATIONS

This application is a continuation-in-part to U.S. patent application Ser. Nos. 12/694,820 filed Jan. 27, 2010, 12/543,785 filed Aug. 19, 2009, and 12/478,300 filed Jun. 4, 2009; the disclosures of which are incorporated herein by reference in their entirety.

BACKGROUND

The invention relates generally to the field of intraoperative nerve imaging and more specifically, to the field of optical design of compact high collection power imaging devices for fluorescence and white light imaging of myelin basic protein (MBP) nerve imaging agents during surgery.

Fluorescence imaging is used to highlight molecules and structures, not otherwise visible under white light illumination, and is an emerging technique for surgical guidance. By administering a molecular contrast agent to a patient, disease processes can be specifically labeled for visualization during clinical examination. In concert with white light imaging, fluorescence imaging captures movies of anatomy with tissue specific information, and provides the clinician with a macroscopic visualization of biology in its intact and native physiological state. It holds promise as a way for real time guidance for tumor resection, sentinel lymph node mapping, vasculature and tissue perfusion imaging, as well as early detection of colorectal cancer.

However, many technical challenges are still present as related to the targeted imaging of nerves. A targeted contrast agent for fluorescence guided surgical imaging of nerves must nominally feature several attributes: the ability to penetrate the blood nerve barrier, high selectivity to nerves, and near infrared fluorescence properties. One issue in imaging nerves is related to the light attenuation in tissue. The spectroscopic properties of the biological medium and the optical properties of the fluorescent contrast agent, which may overlap in the spectral range. Another issue is related to the physics of imaging, a challenge is light attenuation in the nerve tissue and the sensitivity of the imaging instrument at low light conditions.

Imaging of targeted agents requires higher sensitivity to detect low levels of the agent. Regardless of the dose orally, intravascularly, or otherwise administered to the patient, local concentrations of the contrast agent can be on the order of tens of nmol/L.

It is therefore desirable to provide a compact image guided system for intraoperative nerve imagining with high collection power for intraoperative nerve imaging.

BRIEF DESCRIPTION

In one embodiment a system is disclosed for intraoperative nerve imaging during surgery. The system comprises one or more illumination sources, an optical objective, a signal detector and a processor. The illumination sources are capable of producing a visible light and an excitation light tuned to induce fluorescence in an imaging agent that selectively binds to myelin basic protein. The optical objective is capable of directing the visible light and the excitation light in a direction of the surgical site and collecting emitted light; including visible light and at least two fluorescent emission channels.

In one embodiment, the system is employed in an imaging platform for use in open surgical fields. In one embodiment the system is employed in an endoscope or a handheld device.

In still another embodiment, the imaging agent that selectively binds to myelin basic protein may be comprised of a compound of Formula I;

wherein $R^1$ is an alkyl group;
$R^2$ is an electron donating group and $R^3$ is an electron withdrawing group; or
$R^2$ is an electron withdrawing group and $R^3$ is an electron donating group.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the invention relate to a compact dual fluorescence imaging system for open and minimally invasive surgical procedures. Iatrogenic nerve damage can be reduced in cardiovascular and breast cancer surgeries, both of which are predominantly performed as open surgeries, i.e., via large open incisions. For cardiovascular applications such as coronary artery bypass graft surgery (CABG), there is a need to simultaneously visualize the vasculature and the nerves. A precedent exists for using indocyanine green as a blood pool agent. In breast cancer, there is a need to increase contrast, which suffers from partitioning of the agent to adipose tissue. In applications wherein the emission spectrum of the fluorophore is sensitive to the environment ratiometric imaging may discriminate nerve from adipose tissue signal.

A targeted nerve imaging agent for fluorescence guided surgical imaging of nerves must nominally feature several attributes: the ability to penetrate the blood nerve barrier, high selectivity to nerves, and near infrared fluorescence properties.

An agent that selectively binds to myelin basic protein (MBP) may result in increased selectivity in myelin staining and thereby aid in nerve visualization. Successful MBP imaging agents have a number of common attributes including target abundance, high binding affinity for the target, selectivity of the binding agent for the target relative to surrounding tissues, and occupancy. Myelin is a complex mixture composed of approximately 80% lipid fraction and 20% protein fraction. Myelin basic protein (MBP) is a major component of myelin at 5%-15%, which translates into about 5 mM, target concentration and satisfies the abundance criterion. The MBP imaging agents, which are visible by means of fluorescence, may also be referred to as fluorophores.

Motor nerves that are clinically relevant in a surgical setting are highly myelinated. Clinically important sensory nerves, such as the anterior intercostal nerve as well as the cavernous nerves of the prostate, contain myelin.

Shifting the emission wavelength of the MBP imaging fluorophore from the visible to the deep red or near infrared (NIR) may improve visualization of nerves during surgery as operating in the NIR region of the optical spectrum (700-900 nm) as compared to conventional fluorescence imaging in the visible region (450-700 nm). Imaging in the NIR minimizes background autofluorescence, as most of the endogenous fluorescent species (e.g., collagen, elastin, NAD(P)H) emit in the visible spectrum. In addition to water, the tissue constituents that dominate absorption of light in the visible and NIR are hemoglobin, bilirubin, and lipids, which have absorption minima in the red to NIR. Moreover, there is a dramatic decrease in tissue scattering in the NIR relative to visible wavelengths. The reduced absorption and scattering (collectively known as the attenuation coefficient) results in less light attenuation and thus deeper penetration.

In the case of fluorescence image guided surgery, using either an imaging platform for use in open surgical fields or an endoscopic device in minimally invasive surgery, one or more channels may be used to capture the fluorescence emission while a second channel simultaneously captures a color video of the surgical area. Emission in the NIR allows for less spectral overlap between the color and fluorescence channels, resulting in higher color fidelity and higher fluorescence collection efficiency.

In certain embodiments, the MBP nerve imaging agent's absorption and emission may be shifted to the NIR fluorescence region to minimize interference from autofluorescence and maximize depth penetration. In certain embodiments simple spectral unmixing might allow discrimination between nerve and adipose tissue signal intraoperatively.

Figure 1:
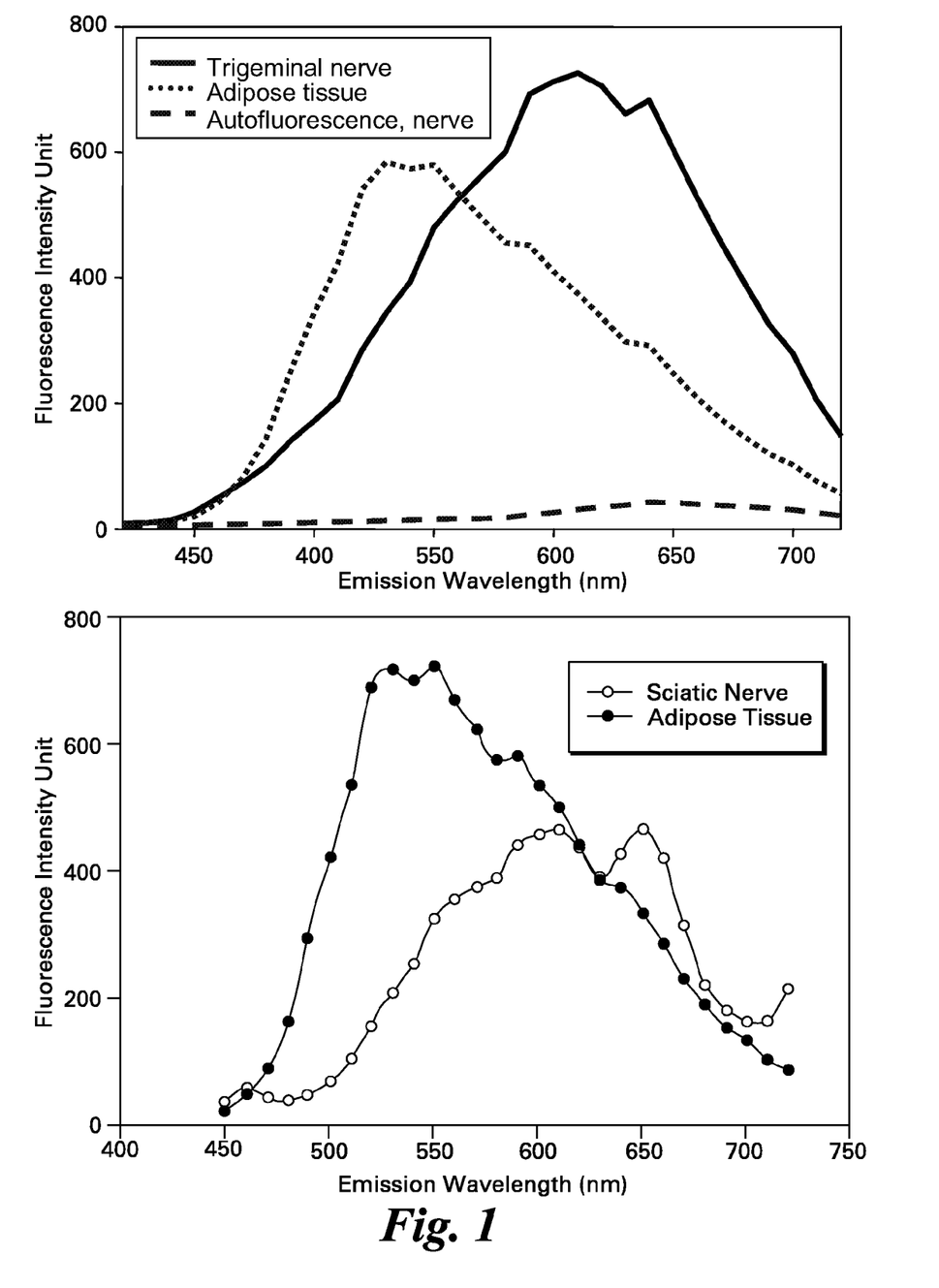
FIG. 1 shows examples of fluorescence emission spectra of adipose tissue and nerve following administration of a myelin basic protein (MBP) targeting fluorophore to a preclinical model.

FIG. 1 shows fluorescence emission spectra of adipose tissue, the trigeminal nerve and the sciatic nerve following systemic injection of a MBP imaging agent . . . . In this example, the MBP imaging agent comprises a compound of Formula I, wherein $R^1$ is $CH_3$, $R^2$ is $NH_2$ and $R^3$ is CN.

Reducing adipose tissue uptake is important, however it is likely that adipose uptake could not be completely eliminated, since the fluorophores need to be lipophilic to allow for penetration into the blood nerve barrier. Therefore, there is a need to discriminate between adipose and nerve fluorescence intraoperatively. In certain embodiments simple spectral unmixing might allow discrimination between nerve and adipose signal intraoperatively. As such, an imaging system capable of two emission channels in the fluorescent region may allow for ratiometric imaging or other forms of spectral discrimination. More specifically it may allow for spectral discrimination of nerve tissues and adipose tissue.

In certain embodiments involving open surgeries, a compact imaging platform capable of imaging two fluorescence emission channels, in addition to real-time color video, may be used. The imaging system may comprise a white light and two fluorescent channels, which has sufficient sensitivity in both fluorescence channels and high color fidelity in the white light channel for adequate rendering of anatomy. This may allow co-registration of anatomic image with fluorescence images in real time.

In certain embodiments, the sensitivity of the system may be determined by collection efficiency, illumination power density at the sample, and overall detector sensitivity. The entrance pupil diameter (EPD) of the primary optics, which determines the numerical aperture (NA), impacts collection efficiency. In a surgical imaging system with a long working distance (e.g., up to 500 mm), the NA may be on the order of 0.01-0.02, resulting in low collection power. The illumination power can be partially increased to compensate for that loss in collection efficiency, but only up to the point of maximum permissible exposure (MPE), dictated by ANSI-Z-136.1. Another practical consideration is limiting the excitation light source to a Class III device (<500 mW exposure in the NIR) to avoid the use of laser interlocks and protective goggles. However, to illuminate a large surgical field of view of 150 mm diameter, the irradiance at the sample provided by a Class III excitation source can be very low (<2.5 mW/cm2). On the detector side, to maintain a compact system design, the detector needs to be also very compact, reducing the pixel size and the possibility of active detector cooling, resulting in low sensitivity.

Because of the broad fluorescence emission spectrum, it is highly likely that the white light channel, covering most of the visible spectrum, will overlap with either the excitation or emission of the fluorescence channel. This effect increases background and diminishes sensitivity in the fluorescence channel(s), and reduces color fidelity in the white light channel. Ambient light in the operating room may also adversely impact image quality, and the addition of a second fluorescence channel exacerbates these challenges. Multi-channel imaging capability may be used to retain or optimize image quality in all three channels.

A simple fixed focus lens may not accommodate a large variation in the working distance (50-500 mm) and field of view (30-150 mm). Furthermore, a zoom lens may be limited in that it has a reduced EPD and thus a reduced optical collection power (collection power scales as EPD-squared.) Also, maintaining a substantial overlap between the illumination spot and imaging field view, and delivering a uniform, unobstructed (shadow-free) illumination over a large working distance is difficult.

Figure 2:
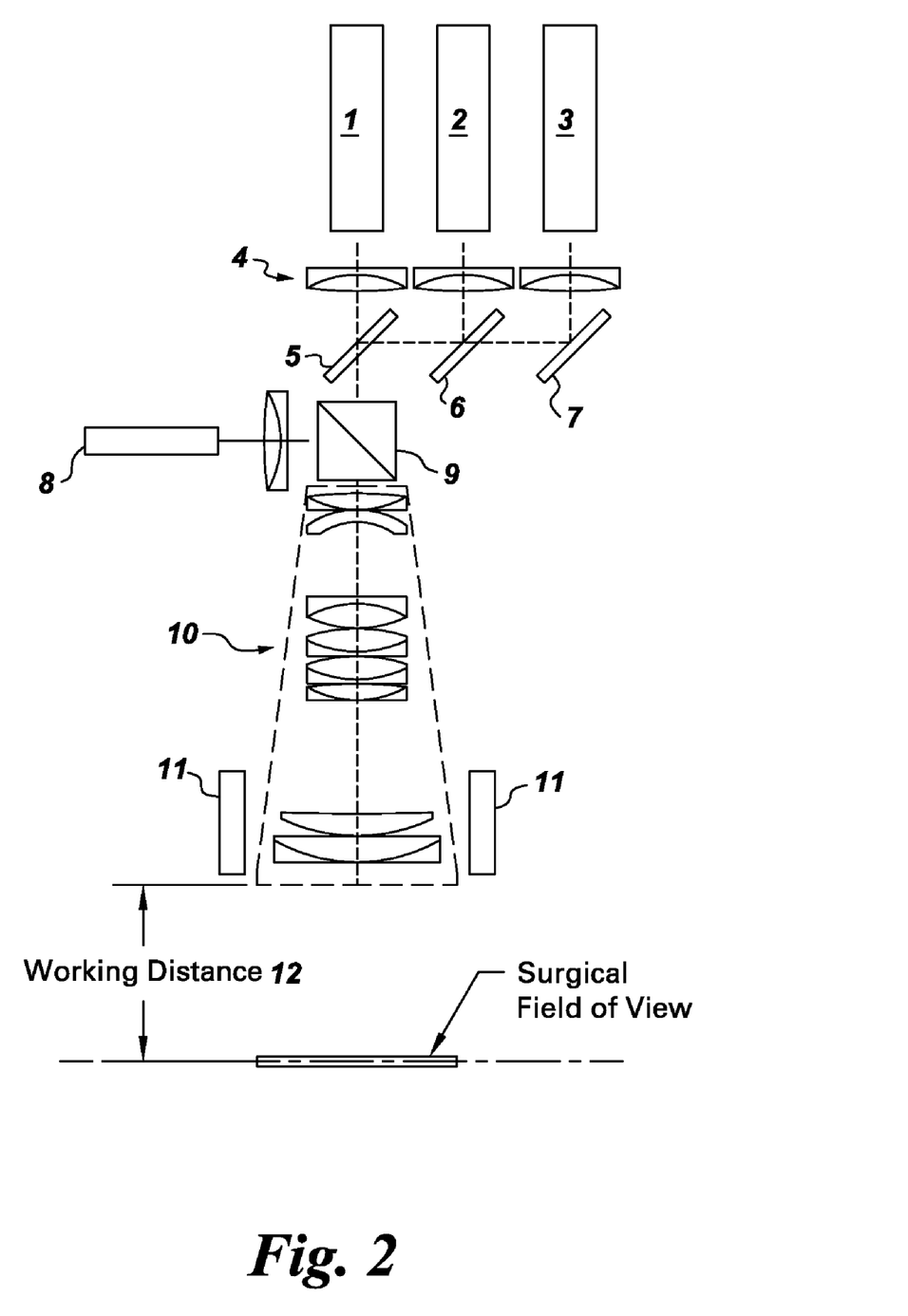
FIG. 2 is a schematic representation of an epi-illumination delivery of laser diode excitation and a zoom lens that maximizes optical collection power.

To overcome these limitations, an embodiment as shown in FIG. 2 may be used in open surgical imaging where an imaging platform is employed. FIG. 2 is a schematic representation of an epi-illumination delivery of laser diode excitation and a zoom lens that maximizes optical collection power. The epi-illumination configuration provides co-registered illumination and imaging field-of-view with maximized the power density within the surgical field-of-view.

The system shown in FIG. 2 comprises two fluorescence charge-coupled device CDD sources (1, 2) as well as white light CCD source (3), a relay lens (4) and dichroic filters (5-7) which are aligned to direct the light into the dichroic filter (9). The dichroic filter operates to selectively transmit light of a certain wavelength on to the surgical site. The dichroic filter also is capable of separating emitted light from the surgical field, into specific wavelengths for detection. A fiber coupled laser source (8) is also positioned to direct light through the filter 9. Zoom lenses, with focus and iris adjustments 10, are positioned downfield of the filter 9. Fiber coupled white light 11 is positioned over the surgical field of view at set working distance from the sample plane 12.

In certain embodiments, the zoom lens 10 may be motorized, allowing for computer control and automation of zoom, focus, and iris adjustment. For example, a compact motorized zoom lens detector may be used such as a 13PZG10×6C DC Iris Compact Zoom Lens (Tamron USA, Inc., Commack, N.Y.). In other embodiments, lens with varying EPD may be used to enhance performance Collection efficiency may be optimized using various basic lens designs including, but not limited to telephoto, retrofocus, afocal zoom lens, and optical compensated PanCinor zoom lens. The lens may be configured for EPD, high zoom ratio and correction for spherical, chromatic, astigmatism, coma, field curvature and other aberrations.

Figure 3:
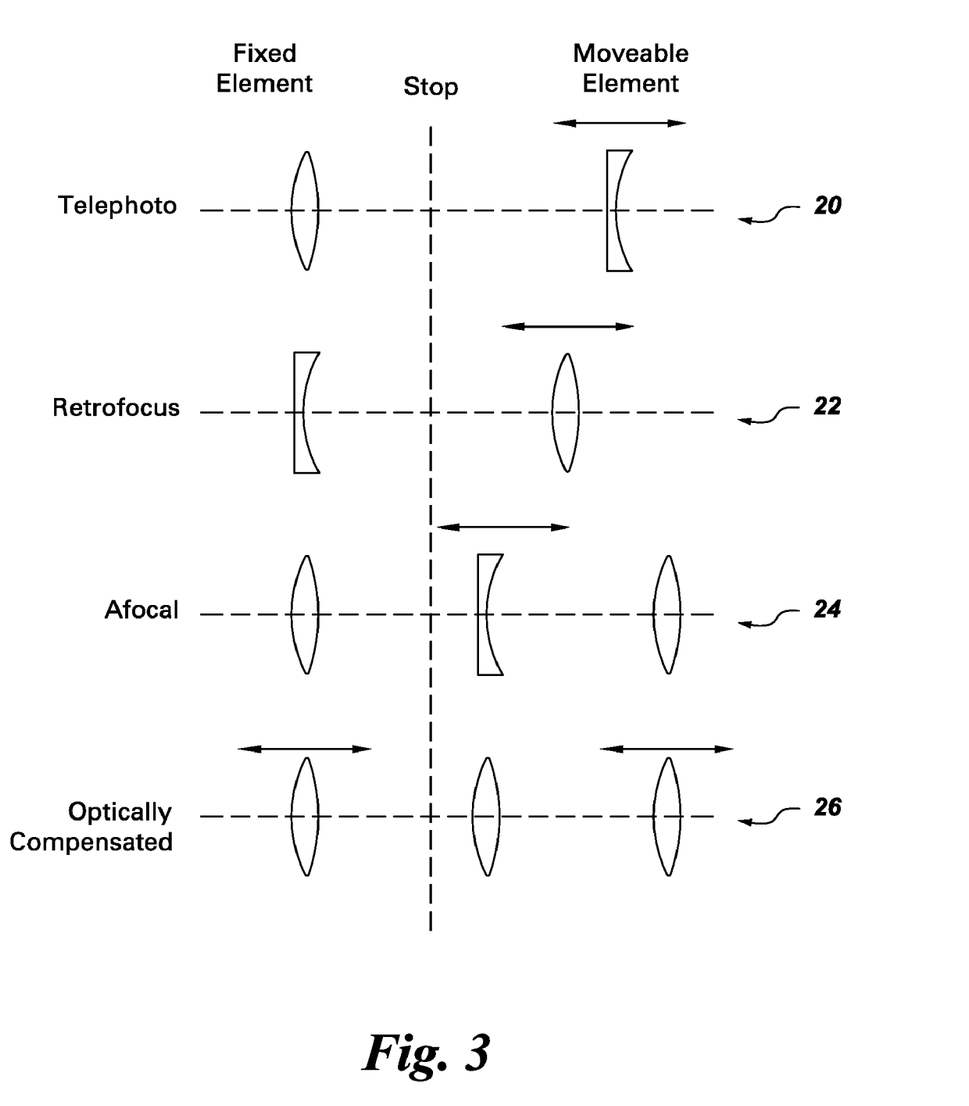
FIG. 3 is a schematic representation of various zoom lens design categories for use in embodiments of the imaging system.

FIG. 3 is a schematic representation of various zoom lens design categories for use in embodiments of the imaging system. The telephoto zoom lens 20 has a positive element close to the object side, followed by a negative element that shifts position to provide different focal length while maintaining the back focus position. The telephoto lens in general has longer focal length and has better correction for a smaller field of view and larger EPD. The retrofocus lens 22 has a reversed configuration where the negative element is closer to the object. It has a shorter focal length and larger field of view (up to 170°) but a smaller EPD, as compared to the telephoto lens, to achieve the same amount of correction for aberrations. The afocal zoom lens 24 consists of a positive element followed by a movable negative element and then another positive element.

In certain embodiments, the addition of a positive element added to this configuration can further optimize the lens design. In still another embodiment, a three element optically compensated zoom lens 26 uses three positive element (two movable element and one fixed position element in the middle) to achieve fixed back focal position zoom.

Various techniques can be applied to the lens configuration to achieve better aberration correction using a minimum number of elements including but not limited to lens bending, aspherical surfaces, high refractive index glass, broken contact element, parallel air space between element with strong curvature to correct for spherical and coma, stop shift theorem (moving location of stop surface) and to correction for spherical, coma, and astigmatism.

In certain embodiments, a time interleaved detection/illumination scheme may be used to minimize the impact of spectral overlapping between fluorescence and white light channel, thus obtaining high color fidelity on the white light color channel. Alternating fluorescence (both channel) and white light image may be captured with synchronized laser and white light illumination. In one embodiment, the resulting image may be displayed at a near video rate, such that the images may be displayed in real time.

Figure 4:
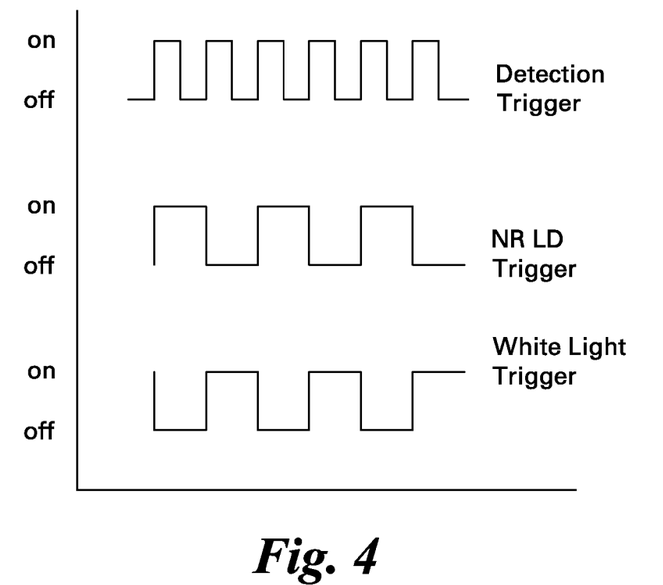
FIG. 4 is a graphical illustration showing triggering the two light sources in a synchronously alternating or out-of-phase fashion at the same frequency, such that, at a given time, the detector may record only either fluorescence or white light image.

One such process is shown in FIG. 4, which illustrates triggering the two light sources in a synchronously alternating or out-of-phase fashion at the same frequency, such that, at a given time, the detector may record only either fluorescence or white light image.

The imaging system may also be part of an imaging device used in minimally invasive surgery (MIS). Minimally invasive surgery is used in a number of surgical applications. The imaging device may be a telescopic instrument such as an endoscope or a handheld device. For example, a radical prostatectomy is the most common surgery performed to treat prostate cancer and may be performed by MIS, such as laparoscopic or robotically assisted prostatectomy, to eliminate the need for a large surgical incision. During laparoscopic prostatectomy, a laparoscope, which is an endoscope for examining the peritoneal cavity, is inserted through small incisions to allow surgeons to visualize inside the abdomen and perform the surgery. As a result, the patient may experience less pain and scarring, faster recovery, and less risk of infection. Nonetheless, despite measures to spare nerves during MIS, nerve damage commonly occurs. Given the emerging utility of MIS in the treatment of prostate cancer, and its persistently high incidence of complications from nerve damage, both surgeries outcomes may be improved by the fluorescence imaging of nerves.

The sensitivity of fluorescence is determined by collection efficiency, detector sensitivity, and excitation light intensity. One of the main challenges of developing a MIS imaging tool capable of dual mode imaging is that a conventional endo scope has a substantially smaller (3-10×) entrance pupil diameter (EPD), which results in significantly lower collection efficiency and sensitivity. Since the EPD is fixed, as determined by the endoscope itself, sensitivity may be improved by focusing on detector sensitivity, and excitation light intensity of the device.

Figure 5:
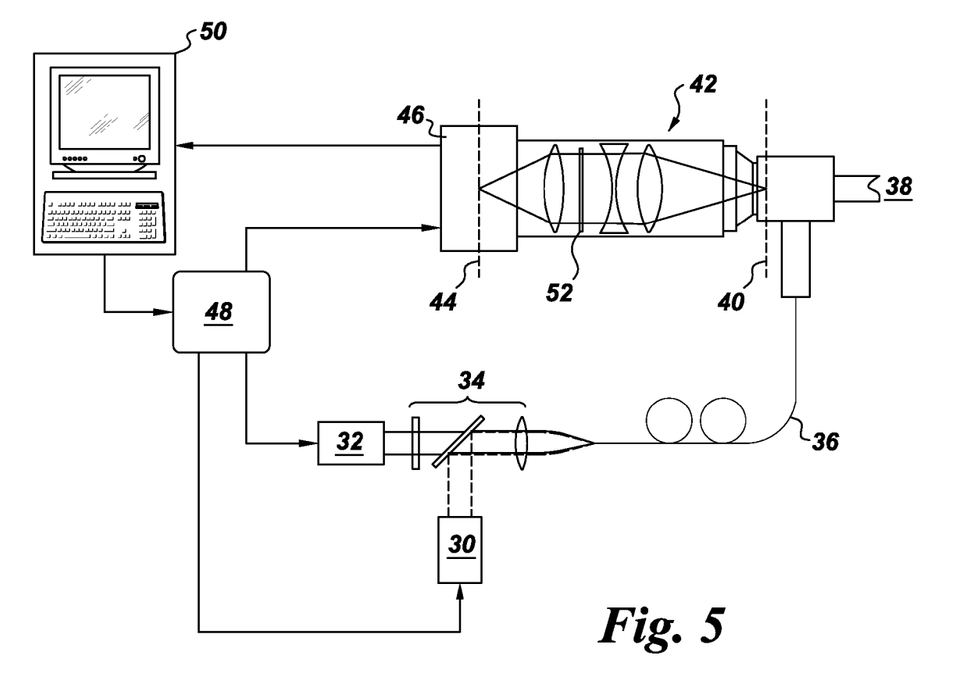
FIG. 5 is a schematic representation of a dual mode system for minimally invasive surgery imaging device.

One embodiment of a dual mode system for minimally invasive imaging device is shown in FIG. 5. As shown, two light sources are used which illuminates the sample out-of-phase synchronously and the detector records images continuously.

As shown further in FIG. 5, for efficient light delivery and illumination, two dedicated light sources for white light and fluorescence imaging may be employed. In certain embodiments, for white-light imaging, an externally triggerable white light or red-green-blue (RGB) light emitting diode 30 may be used while for fluorescence, a high power laser diode 32 emitting at the optimized wavelength for the maximum absorption of the specific MBP imaging dye may be used. Both sources may be tuned to deliver a specific wavelength.

Light from the two light sources may be combined with either free space dichroic beam combiner or a fiber-based beam combiner 34. The choice of beam delivery method may be determined by efficiency of light delivery. The combined beams may be coupled into the standard light guide 36, for example a 495 NCS light cable, diameter 4.8 mm (Karl Storz, Tuttlingen, Germany), which is capable of connecting to the light delivery port of conventional endo scope such as a laparoscopes 38. An external pulse generator 48 may be used to trigger the two light sources.

As shown earlier in FIG. 4, process may be used for triggering the two light sources in a synchronously alternating or out-of-phase fashion at the same frequency, such that, at a given time, the detector may record only either fluorescence or white light image.

Referring again to FIG. 5, in certain embodiments, imaging lenses 42 may be configured to relay the image formed in the intermediate image plane 40 by the endoscope onto a the detector imaging plane 44 of the detector 46, which may then be relayed to processor and imaging device 50. The lenses may be designed and fabricated to achieve high-contrast images. In addition to the lenses, optical filter may be used such as, but not limited to, a laser rejection filter, emission filter, notch filter or in various combinations thereof.

Figure 6:
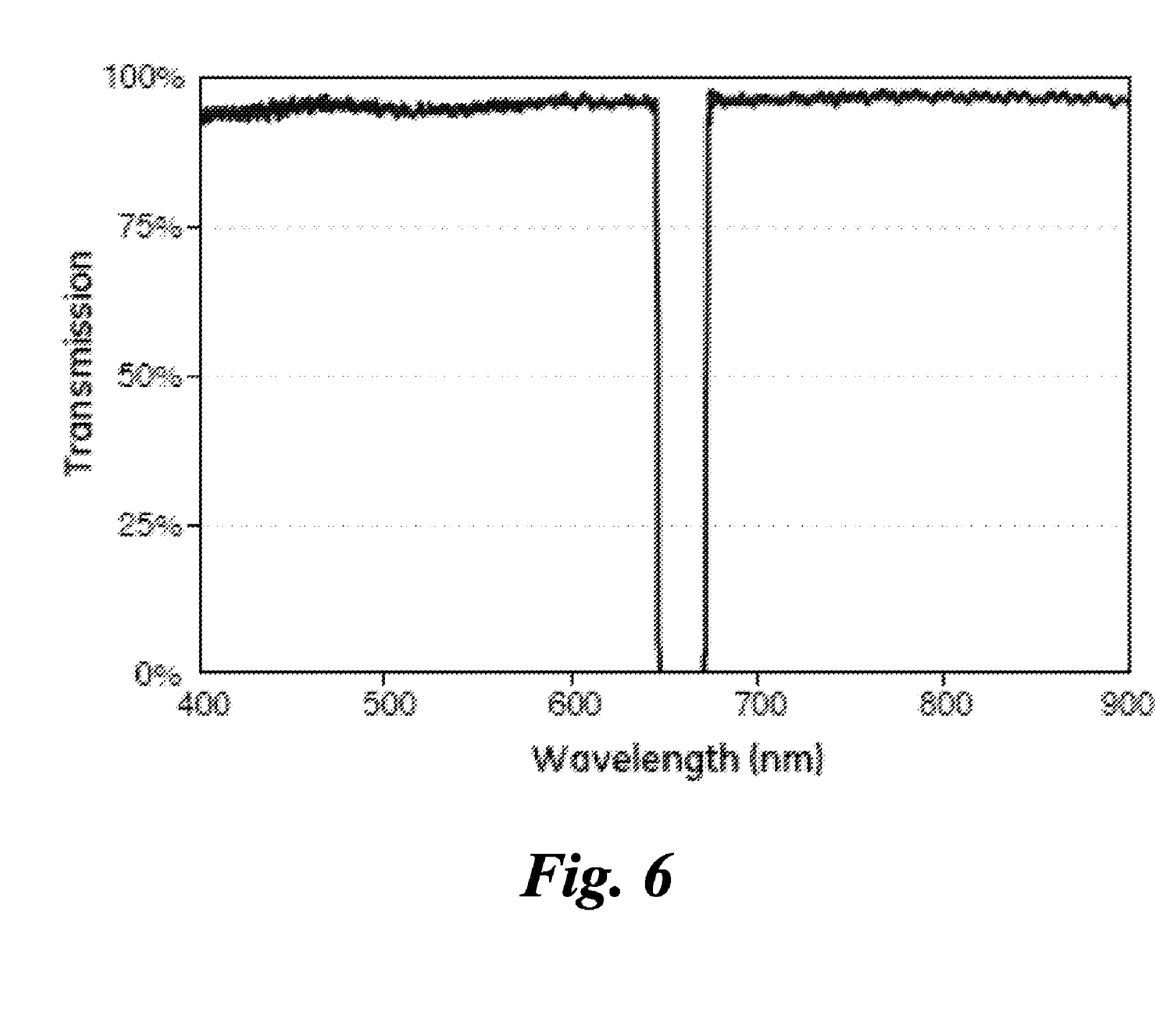
FIG. 6 is an example of a notch filter transmission spectrum.

In certain embodiments, a notch filter 52 may be inserted in the light path where the beams are collimated. The notch filter is employed to block the back-reflected light from the sample under the illumination of the excitation light source. The use of a notch filter does not degrade white light image significantly, as it is in the near-infrared regime and its spectral band is narrow (<25 nm). An example of a notch filter transmission spectrum is shown in FIG. 6. The spectrum shown in a typical transmission spectrum of a commercial notch filter (StopLine® Thin-film Single Notch Filter NF03-658E-25, Semrock Inc., Rochester N.Y.) with a 27 nm notch bandwidth centered at 658 nm. The filter features an optical density greater than 6 in the notch and greater than 95% transmission for most other wavelengths in the visible and NIR.

In certain embodiments, a hybrid refractive-diffractive element is employed to increase the entrance pupil diameter (EPD) of a wide-angle fisheye lens, thus achieving higher collection power and maintaining small overall diameter. The EPD of the objective may be greater than about 0.6 mm. Collection power of a lens is proportional to the square of the EPD, therefore, the objective of the invention has about 9 to 25 times higher collection power than conventional endoscope objectives which have EPD of about 0.2 mm. In certain embodiments, the objective is adapted to capture fluorescence signal for visible or near infrared wavelengths, or both.

In certain embodiments, the endoscope objective employs a negative meniscus lens having a first surface and a second surface; a stop adjacent to the negative meniscus lens; a positive lens adjacent to the negative lens and having a first surface and a second surface; and a hybrid refractive-diffractive element adjacent to the positive lens and having a first surface and a second surface, wherein one of the first surface, or the second surface comprises a diffractive surface, wherein the objective has an effective focal length in a range from about 0.8 mm to about 1.6 mm. The term "adjacent to" encompasses instances where a gap may exist between the two elements that are being referred to as being adjacent to, that is, the two elements may not be in physical contact. In one embodiment, the stop is located adjacent to the second surface of the negative meniscus lens. In one embodiment, the positive lens is disposed adjacent to the stop such that the first surface of the positive lens is closer to the stop. In one embodiment, the hybrid refractive-diffractive element is disposed adjacent to the positive lens.

In certain embodiments, the objective may have an effective focal length in a range from about 0.8 mm to about 1.6 mm. As used herein the term "effective focal length" refers to the distance from the principal point to the focal point. The focal length of an optical system is a measure of how strongly the system converges (focuses) or diverges (defocuses) light. A system with a shorter focal length has greater optical power than one with a long focal length; that is, it bends the pencil of rays more strongly, bringing them to a focus in a shorter distance. For applications, such as endoscopy where it is desirable to have a large angular field-of-view, it is desirable to have small effective focal length. In one embodiment, the effective focal length of the hybrid refractive-diffractive element is greater than about 1 mm. In certain embodiments, a full field of view (FFOV) of the endoscope is in a range from about 60 degrees to about 170 degrees.

Figure 7:
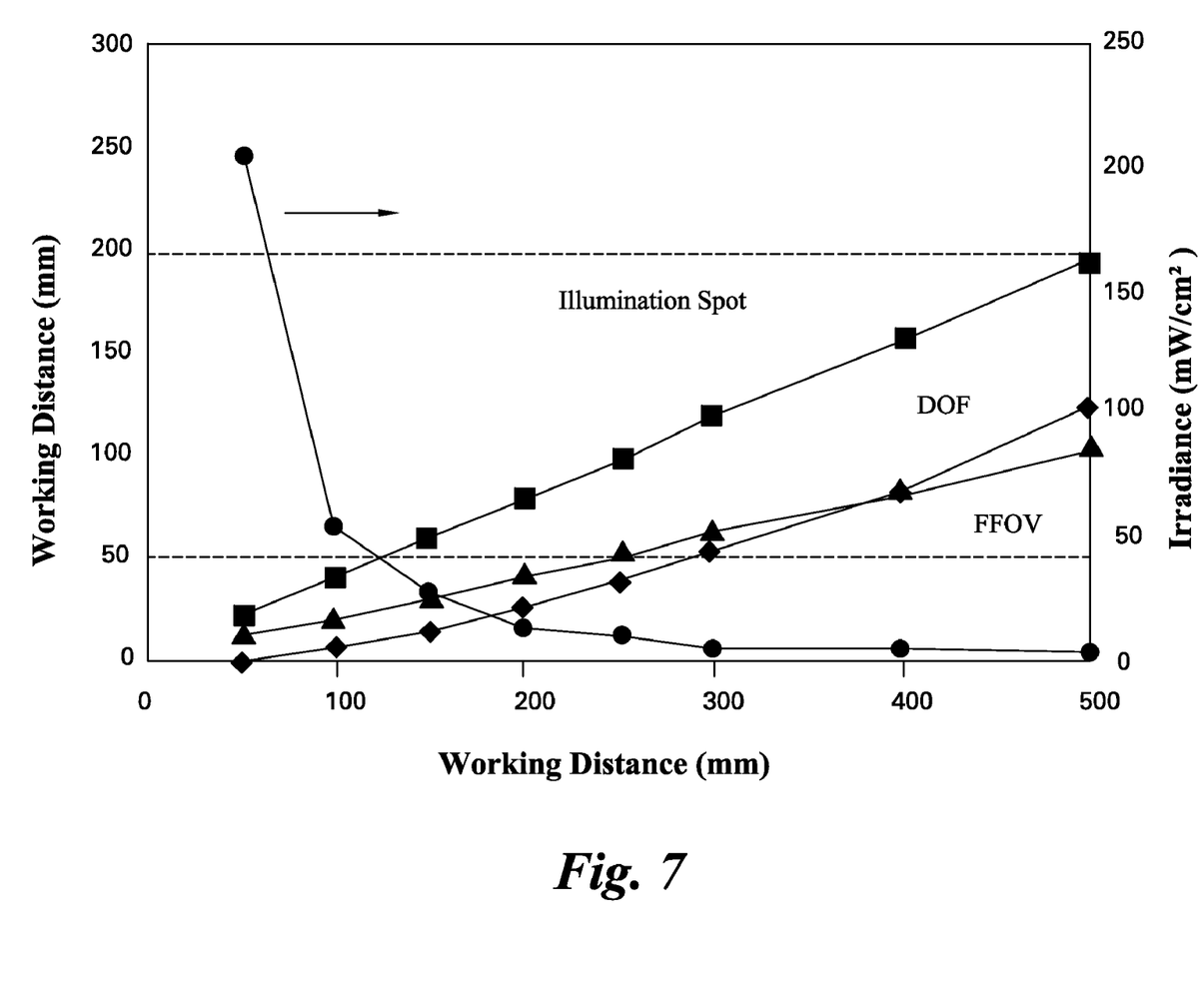
FIG. 7 is a graphical representation of the theoretical performance parameters of an endo scope are shown as a function of working distance.

Theoretical performance parameters of an endoscopic device are shown as a function of working distance (WD) in FIG. 7. Irradiance at the sample drops geometrically with distance, while the illumination spot diameter, depth of field (DOF), and imaging full field of view (FFOV) increase linearly with WD. Using the laser diode excitation source, the irradiance at the sample can provide adequate excitation power density (5 mW/cm$^2$) at up to 300 mm WD. Optimized for a typical WD of 150 mm, the DOF is 15 mm, defined by the location where the modulation transfer function (MTF) drops by 15% relative to best focus. While 15 mm seems somewhat limited, a low DOF is a consequence of increasing the EPD. Furthermore, the image quality can be acceptable over a wider range, as a 15% drop in the MTF is quite stringent and maintains images with fairly high image quality.

It may be desirable to use an array detector that is lightweight and sensitive. This may be achieved by use of a compact, actively cooled, electron-multiplying charge coupled device (EMCCD) camera (RT-XMV-246RGB-C, Retriever Technology, N. Mex., USA). The camera may be externally triggered at twice the frequency of the light source trigger, such that it is capable of recording white and fluorescence images continuously. Furthermore, since in certain applications a lower signal level for the fluorescence mode is obtained as compared to white light detection (RBG range), the detector may be adjusted to selectively improve the fluorescence detection sensitivity. The optimum gain may vary according to the specific application and may be approximated using imaging fluorescence samples in tissue-mimicking phantoms (e.g., fluorescence inclusions in a 1%-2% Intralipid solution).

The imaging hardware may be modified as required by the in vivo properties of the nerve imaging agent. The excitation wavelength may be temperature-tuned to determine the optimal excitation wavelength. If the optimal wavelength exceeds the tunable range of the excitation laser diode (roughly 5-10 nm), the diode may be replaced with a more appropriate wavelength. Several vendors (e.g. PLT Technologies, Santa Barbara, Calif.) provide a wide selection of high power laser diodes at various wavelengths in the red to NIR. Accordingly, the excitation filter, dichroic and emission filters may also be replaced. In vivo imaging will be used to optimize the software for ratiometric imaging.

In certain embodiments, the specific binding to myelin basic protein may be by an agent comprising the compound of Formula I, wherein $R^1$ is an alkyl group, $R^2$ is an electron donating group and $R^3$ is an electron withdrawing group, or $R^2$ is an electron withdrawing group and $R^3$ is an electron donating group.

In certain embodiments $R^1$ may be a lower alkyl groups of from 1 to 6 carbon atoms, preferably from 1 to 4 carbon atoms, and includes methyl, ethyl, n-propyl, isopropyl, and n-, s- and t-butyl. The electron donating group may include a primary, secondary, or tertiary amine (—NH$_2$, NHR, NR'R"), or an alkoxy group (—OR). The electron withdrawing group may include a nitrile group (—CN), an ester (—COOR), or a sulfone (—SO$_2$R).

In each embodiment, $R^2$ and $R^3$ are conjugated through the π double bond orbitals of the benzene rings and olefinic substituents, thereby providing a clear path for electrons to flow from the electron-donating group to the electron-withdrawing group. The electron-donating group may be in the $R^2$ or $R^3$ position provided that an electron-withdrawing group is in the alternative position.

In certain embodiments, $R^1$ is an alkyl group, $R^2$ is an electron donating group and $R^3$ is a —$SO_2R^4$ group wherein $R^4$ is a is an alkyl, substituted alkyl, amine, or substituted amine group. In certain embodiments $R^1$ may be a lower alkyl groups of from 1 to 6 carbon atoms, preferably from 1 to 4 carbon atoms, and includes methyl, ethyl, n-propyl, isopropyl, and n-, s- and t-butyl. The electron donating group may include a primary, secondary, or tertiary amine, or an alkoxy group. $R^4$ may be lower alkyl groups of from 1 to 6 carbon atoms, preferably from 1 to 4 carbon atoms, and includes methyl, ethyl, n-propyl, isopropyl, and n-, s- and t-butyl.

In other embodiments, $R^4$ may be used to improve water solubility and reduce logP of the resulting sulfone. $R^4$ may be a substituted alkyl group, such as, but not limited to an alkoxy or alcohol. In certain embodiments, the alkoxy group may contain ethylene glycol units or an ethylene glycol terminated alcohol. For example $R^4$ may be $(CH_2CH_2O)_nX$ or $CH_2CH_2CH_2(OCH_2CH_2)_nOX$ where n is an integer between 1 and 6 and X is hydrogen, methyl or ethyl. The incorporation of a propyl group may also eliminate the potential for β elimination In certain other embodiments, $R^4$ may be a primary, secondary, or tertiary amine to form a sulfonamide. The amine groups include, but are not limited to $NH_2$, $NHR^5$ and $NR^5R^6$ wherein $R^5$ and $R^6$ are alkyl or substituted alkyl groups. $R^5$ and R6 may or may not be equivalent and may form a ring structure. For example $R^5$ and R6 may be $(CH_2CH_2O)_nX$ or $CH(CH_2OX)_2$, $C(CH_2OX)_3$ where n is an integer between 1 and 6 and X is hydrogen, methyl, or ethyl. In other examples $R^5$ and R6 may from a ring structure such as a substituted piperidine, piperazine, or morpholine.

In each embodiment, $R^2$ and —$SO_2R^4$ are conjugated through the π double bond orbitals of the benzene rings and olefinic substituents, thereby providing a clear path for electrons to flow from the electron donating group to the electron withdrawing group.

This conjugation and "push-pull" electron flow from $R^2$ to $R^3$, as well as $R^2$ to —$SO_2R_4$ may be responsible for a Stokes shift of a longer wavelength during fluorescence as compared to similar heterocyclic compounds. In applications, this may allow enhanced contrast between myelin and surrounding tissue when using an agent of Formula I.

Various means exist for applying the nerve imaging agent to the surgical site. These methods include, but are not limited to, intravenous injection, intraperitoneal injection, subcutaneous injection, intramuscular injection, intrathecal injection, intracerebral injection, intracerebroventricular injection, intraspinal injection, or combinations thereof.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A system for intraoperative nerve imaging during surgery, comprising:
   one or more illumination sources for producing a visible light and an excitation light, wherein the excitation light is configured to induce fluorescence in an agent that selectively binds to myelin basic protein applied to a surgical site;
   an optical objective for directing the visible light and the excitation light in a direction of the surgical site and collecting visible light and fluorescent light emitted in at least two fluorescent emission channels from the surgical site;
   a signal detector in operative association with the optical objective capable of detecting the visible light and fluorescent light; and
   a signal processor for processing signals corresponding to the visible light and the fluorescent light emitted in at least two fluorescent emission channels from the surgical site.

2. The system of claim 1 wherein at least one of the fluorescent emission channels tuned to image is between 450-900 nm.

3. The system of claim 1 wherein at least one of the fluorescent emission channels is between 700-900 nm.

4. The system of claim 1 wherein the at least two fluorescent emission channels allows for spectral discrimination of nerve tissue and adipose tissue.

5. The system of claim 1 wherein the processor is further capable of reconstructing images of the surgical field from the signals obtained from the signal detector and wherein said images are registered and displayed on a display device in operative association with the processor.

6. The system of claim 5 wherein the processor is further capable of multi-channel image capture using synchronized laser and white light illumination and detection.

7. The system of claim 6 wherein images are displayed at a near video rate.

8. The system of claim 1, wherein the optical objective is employed in an imaging platform for use in open surgical fields.

9. The system of claim 8 wherein the optical objective comprises an epi-illumination delivery system, said epi-illumination delivery system comprising;
   a dichroic filter fiber coupled to the laser light source, said filter capable of selectively transmitting light having a specific wavelength, separating emitted light into specific wavelengths, or a combination thereof; and
   one or more lenses capable of focus adjustments positioned between the dichroic filter and the surgical field.

10. The system of claim 9 wherein the lenses comprises telephoto, retrofocus, afocal zoom lens, optical compensated PanCinor zoom lens, or combinations thereof.

11. The system of claim 9 wherein the illumination sources comprises a laser light source coupled to the dichroic filter and a fiber coupled white light source positioned above the surgical field.

12. The system of claim 1, wherein the optical objective is employed in an endoscope or a handheld device.

13. The system of claim 12 wherein the optical objective comprises:
   a negative meniscus lens having a first surface and a second surface;
   a stop adjacent to the negative meniscus lens;
   a positive lens adjacent to the negative lens and having a first surface and a second surface;
   a hybrid refractive-diffractive element adjacent to the positive lens and having a first surface and a second surface, wherein one of the first surface, or the second surface comprises a diffractive surface, and
   wherein the objective has an effective focal length in a range from about 0.8 mm to about 1.6 mm.

14. The system of claim 13 wherein the optical objective further comprising an optical filter comprising wherein said optical filter is a laser rejection filter, emission filter, notch filter or combination thereof.

15. The system of claim 12 wherein the one or more illuminating sources comprises a white light emitting diode and a laser diode said diodes capable of being operated in an alternating fashion.

16. The system of claim 12 wherein the detector is an array detector capable of detecting white light and fluorescent light continuously.

17. The system of claim 1 wherein the agent that selectively binds to myelin basic protein comprises:
a compound of Formula I;

wherein $R^1$ is an alkyl group;

$R^2$ is an electron donating group and $R^3$ is an electron withdrawing group; or $R^2$ is an electron withdrawing group and $R^3$ is an electron donating group.

18. The system of claim 17 wherein:
$R^1$ is a lower alkyl group of from 1 to 6 carbon atoms;
the electron donating group is a primary amine, secondary amine, tertiary amine, or alkoxy; and
the electron withdrawing group is a nitrile group or an ester.

19. The system of claim 18 wherein:
$R^1$ is an lower alkyl group from 1 to 6 carbon atoms;
$R^2$ is an electron donating group; and
$R^3$ is —$SO_2R^4$ wherein $R^4$ is an alkyl, substituted alkyl, amine or substituted amine.

20. The system of claim 1 wherein the agent is applied to the surgical site by intravenous injection, intraperitoneal injection, subcutaneous injection, intramuscular injection, intrathecal injection, intracerebral injection, intracerebroventricular injection, intraspinal injection, or combinations thereof.

* * * * *

UNITED STATES PATENT AND TRADEMARK OFFICE
CERTIFICATE OF CORRECTION

| | | |
|---|---|---|
| PATENT NO. | : 8,169,696 B2 | Page 1 of 1 |
| APPLICATION NO. | : 12/821731 | |
| DATED | : May 1, 2012 | |
| INVENTOR(S) | : Yazdanfar et al. | |

It is certified that error appears in the above-identified patent and that said Letters Patent is hereby corrected as shown below:

ON THE TITLE PAGE:

Item (74), under "Attorney, Agent, or Firm", in Column 2, Line 1, delete "Gallegher" and insert -- Gallagher --, therefor.

IN THE SPECIFICATIONS:

In Column 5, Line 10 delete "CDD" and insert -- CCD --, therefor.

In Column 8, Line 66, delete "it" and insert -- $\pi$ --, therefor.

In Column 9, Line 21, delete "$(CH2_2CH_2O)_nX$" and insert -- $(CH_2CH_2O)_nX$ --, therefor.

In Column 9, Line 31, delete "$_nX$ or" and insert -- $_nX$, or --, therefor.

IN THE CLAIMS:

In Column 10, Line 33, in Claim 9, delete "comprising;" and insert -- comprising: --, therefor.

Signed and Sealed this
Twenty-sixth Day of June, 2012

David J. Kappos
*Director of the United States Patent and Trademark Office*